(12) United States Patent
deKemp

(10) Patent No.: US 8,071,959 B2
(45) Date of Patent: Dec. 6, 2011

(54) RUBIDIUM GENERATOR FOR CARDIAC PERFUSION IMAGING AND METHOD OF MAKING AND MAINTAINING SAME

(75) Inventor: Robert A deKemp, Ottawa (CA)

(73) Assignee: Ottawa Heart Institute Research Corp., Ottawa (CA)

( * ) Notice: Subject to any disclaimer, the term of this patent is extended or adjusted under 35 U.S.C. 154(b) by 1356 days.

(21) Appl. No.: 11/312,368

(22) Filed: Dec. 21, 2005

(65) Prior Publication Data

US 2007/0140958 A1    Jun. 21, 2007

(51) Int. Cl.
*A61K 51/00* (2006.01)

(52) U.S. Cl. ..... 250/435; 250/428; 250/430; 250/432 R; 250/436; 250/432 PD

(58) Field of Classification Search .................. 250/428, 250/430, 432 R, 435, 436, 432 PD
See application file for complete search history.

(56) References Cited

U.S. PATENT DOCUMENTS

| | | | | |
|---|---|---|---|---|
| 2,845,136 A | * | 7/1958 | Robinson | 96/107 |
| 3,164,980 A | * | 1/1965 | Loyd | 73/23.39 |
| 3,935,884 A | * | 2/1976 | Hazelton | 141/80 |
| 3,969,243 A | * | 7/1976 | Arion | 210/662 |
| 4,175,037 A | * | 11/1979 | Benney et al. | 141/12 |
| 4,193,867 A | * | 3/1980 | Evans | 210/661 |
| 4,379,855 A | * | 4/1983 | Down et al. | 521/26 |
| 4,400,358 A | | 8/1983 | Neirinckx | 423/2 |
| 4,406,877 A | | 9/1983 | Neirinckx et al. | 424/1.1 |
| 4,562,829 A | | 1/1986 | Bergner | 128/1.1 |
| 4,585,009 A | | 4/1986 | Barker et al. | 128/655 |
| 4,585,941 A | | 4/1986 | Bergner | 250/363 |
| 5,545,319 A | * | 8/1996 | Hart et al. | 210/279 |
| 5,693,223 A | * | 12/1997 | Yamada et al. | 210/198.2 |
| 6,157,036 A | * | 12/2000 | Whiting et al. | 250/432 PD |
| 6,197,174 B1 | * | 3/2001 | Barber et al. | 204/524 |
| 6,908,598 B2 | | 6/2005 | Sylvester | 423/2 |
| 7,476,377 B2 | * | 1/2009 | Moller et al. | 423/598 |
| 2003/0073854 A1 | * | 4/2003 | Zoeller et al. | 549/315 |

OTHER PUBLICATIONS

Alvarez-Diaz et al., "manufacture of strontium-82/rubidium-82 generators and quality control of rubidium-82 chloride for myocardial perfusion imaging in patients using positron emission tomography", Applied Radiation and Isotopes, vol. 50, No. 6, 1999, pp. 1015-1023.*

(Continued)

*Primary Examiner* — Robert Kim
*Assistant Examiner* — Michael Logie
(74) *Attorney, Agent, or Firm* — McCarthy Tétrault LLP; Anita Nador

(57) ABSTRACT

An $^{82}$Sr/$^{82}$Rb generator column is made using a fluid impervious cylindrical container having a cover for closing the container in a fluid tight seal, and further having an inlet for connection of a conduit for delivering a fluid into the container and an outlet for connection of a conduit for conducting the fluid from the container. An ion exchange material fills the container, the ion exchange material being compacted within the container to a density that permits the ion exchange material to be eluted at a rate of at least 5 ml/min at a fluid pressure of 1.5 pounds per square inch (10 kPa). The generator column can be repeatedly recharged with $^{82}$Sr. The generator column is compatible with either three-dimensional or two-dimensional positron emission tomography systems.

5 Claims, 4 Drawing Sheets

OTHER PUBLICATIONS

Brihaye et al. "preparation and evaluation of a hydrous tin(IV) oxide 82Sr/82Rb medical generator system for continuous elution", International Journal of Radiation Applications and instrumentation. Part A. Applied Radiation and Isotopes vol. 38, Issue 3, 1987, pp. 213-217.*

International Search Report dated Apr. 17, 2007, issued on corresponding International Patent Application Serial No. PCT/CA2006/002043.

Alverez-Diaz, Teresa M. et al. Manufacturing of strontium-82/rubidium-82 generation and quality control of rubidium-82 chloride for myocardial perfusion imaging in patients using position emission tomography, Applied Radiation and Isotopes, vol. 50, No. 6, 1999, pp. 1015-1023.

Yano, Y. et al., Rubidium-82 Generators for Imaging Studies, The Journal of Nuclear Medicine, vol. 18, No. 1, 1977, pp. 46-50.

* cited by examiner

RUBIDIUM GENERATOR FOR CARDIAC PERFUSION IMAGING AND METHOD OF MAKING AND MAINTAINING SAME

CROSS-REFERENCE TO RELATED APPLICATIONS

This is the first application filed for the present invention.

MICROFICHE APPENDIX

Not Applicable.

TECHNICAL FIELD

The present application relates in general to nuclear medicine and, in particular, to a rubidium generator for cardiac perfusion imaging and method of making and maintaining same.

BACKGROUND OF THE INVENTION

As is well known in the art, $^{82}$Rb is used as a positron emission tomography (PET) tracer for measurement of myocardial perfusion (blood flow) in a non-invasive manner.

Recent improvements in PET technology have introduced 3-dimensional positron emission tomography (3D PET). Although 3D PET technology may permit more efficient diagnosis and prognosis in patients with suspected coronary artery disease, the sensitivity of 3D PET requires very accurate control of the delivery of $^{82}$R activity to a patient being assessed.

As is well understood in the art, $^{82}$Rb for myocardial perfusion imaging is produced using a strontium-rubidium ($^{82}$Sr/$^{82}$Rb) generator which is eluted using a sterile saline solution (0.9% Sodium Chloride Injection) to produce an $^{82}$Rb eluate ([$^{82}$Rb] Rubidium Chloride Injection) that is injected into the patient during the PET imaging. Due to the above-noted sensitivity of 3D PET it is desirable to deliver the $^{82}$Rb elution to the patient as far away from the patient's heart as can be practically achieved. This is best accomplished by using a small vein in the patient's hand, for example, as the $^{82}$Rb elution injection site. Doing so, however, requires a low pressure, low flow rate elution and precision flow control.

There therefore exists a need for an $^{82}$Rb generator that enables low pressure elution and facilitates precision flow control of patient elution injections.

SUMMARY OF THE INVENTION

It is therefore an object of the invention to provide a rubidium generator column that enables low pressure elution and facilitates precision flow control of patient elutions.

The invention therefore provides a method of preparing an $^{82}$Sr/$^{82}$Rb generator column for low pressure elution, comprising: filling the generator column with an ion exchange material that tightly binds $^{82}$Sr but not $^{82}$Rb, and compacting the ion exchange material to a density that permits fluid solutions to be pumped through the generator column at a rate of at least 5 ml/min at a fluid pressure of 1.5 pounds per square inch (10 kPa); conditioning the ion exchange material; and loading the generator column with a solution of $^{82}$Sr.

The invention further provides an $^{82}$Sr/$^{82}$Rb generator column, comprising: a fluid impervious cylindrical container having a cover for closing the container in a fluid tight seal, and further having an inlet for connection of a conduit for delivering a fluid into the container and an outlet for connection of a conduit for conducting the fluid from the container; and an ion exchange material filling the container, the ion exchange material being compacted within the container to a density that permits the ion exchange material to be eluted at a rate of at least 5 ml/min at a fluid pressure of 1.5 pounds per square inch (10 kPa).

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

The present invention provides an $^{82}$Sr/$^{82}$Rb generator column for use in positron emission tomography cardiac perfusion imaging. In accordance with the invention, the generator column is filled with an ion exchange material that tightly binds $^{82}$Sr but not $^{82}$Rb. The ion exchange material is compacted to a density that permits fluid solutions to be pumped through the generator column at a rate of at least 5 ml/min at a fluid pressure of 1.5 pounds per square inch (10 kPa). After the generator column is packed with the ion exchange material, it is conditioned with a source of excess sodium cations and loaded with a solution of $^{82}$Sr. The generator column in accordance with the invention enables low pressure injections using a peristaltic pump and facilitates precision flow control of patient elutions. Advantageously, the generator column in accordance with the invention can also be reloaded with $^{82}$Sr a plurality of times. This has distinct advantages. First, residue $^{82}$Sr remaining in the column from a previous load is not wasted. Second, the expense of building and conditioning the generator column is distributed over a plurality of $^{82}$Sr loads, so the overall cost of using, $^{82}$Rb for cardiac perfusion imaging is reduced.

Figure 1:
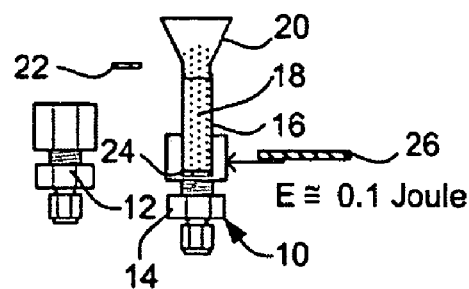
FIG. 1 is a schematic diagram illustrating the packing of a generator column in accordance with the invention.

FIG. 1 illustrates the packing of an $^{82}$Rb generator column 10 using a method in accordance with the invention. As is known in the art, the generator column 10 is constructed from stainless steel hardware components that are commercially available. In the embodiment shown in FIG. 1, a pair of SWAGELOK® reducing adaptors with nuts and ferrules 12, 14 are connected to opposite ends of a stainless tubing 16 that is packed with an ion exchange material 18. In one embodiment of the invention, the ion exchange material 18 is an α-hydrous tin dioxide (Sno$_2$.xH$_2$O, where x equals 1-2) wetted with a NH$_4$OH/NH$_4$Cl buffer (pH 10).

A 25 micron filter 24 closes a bottom of the cylinder 16 at an outlet end thereof. Likewise, a 25 micron filter 22 closes an inlet end of the cylinder 16 after the cylinder 16 is packed with the ion exchange material 18. A feature of the invention is that, unlike prior art generator columns in which the ion exchange material is tightly packed so that high pressure elution is required, the ion exchange material 18 is packed only to a density that permits fluid solutions to be pumped through the generator column at a rate of at least: 5 ml/min at a fluid pressure of 1.5 pounds per square, inch (10 kPa). As shown in FIG. 1, a simple and practical way of accomplishing, the required packing of the ion exchange material 18 is to repeatedly strike a side of the generator column 10 with an instrument 26, such as a laboratory wrench, with a force that exerts about 0.1 Joule. Experience has shown that between 50 and 100 strikes are required to achieve the required density of the ion exchange material 18.

After packing of the generator column 10 is complete, a funnel 20 that was used to introduce the ion exchange material 18 into the cylinder 16 is removed and the ion exchange material is leveled with the top of the cylinder 16. The ion exchange material packed into the generator column 10 has a density of not more than 3 g/cm$^3$ in the packed state. The filter 22 is then placed on top of cylinder 16 and the SWAGELOK adapter, nut and ferrule 12 is secured to the top of the cylinder in a manner well known in the art. As will be understood by those skilled in the art, the generator column 10 in accordance with the invention is constructed under sterile conditions using sterile components and may be pressure tested for leaks after assembly.

Figure 2:
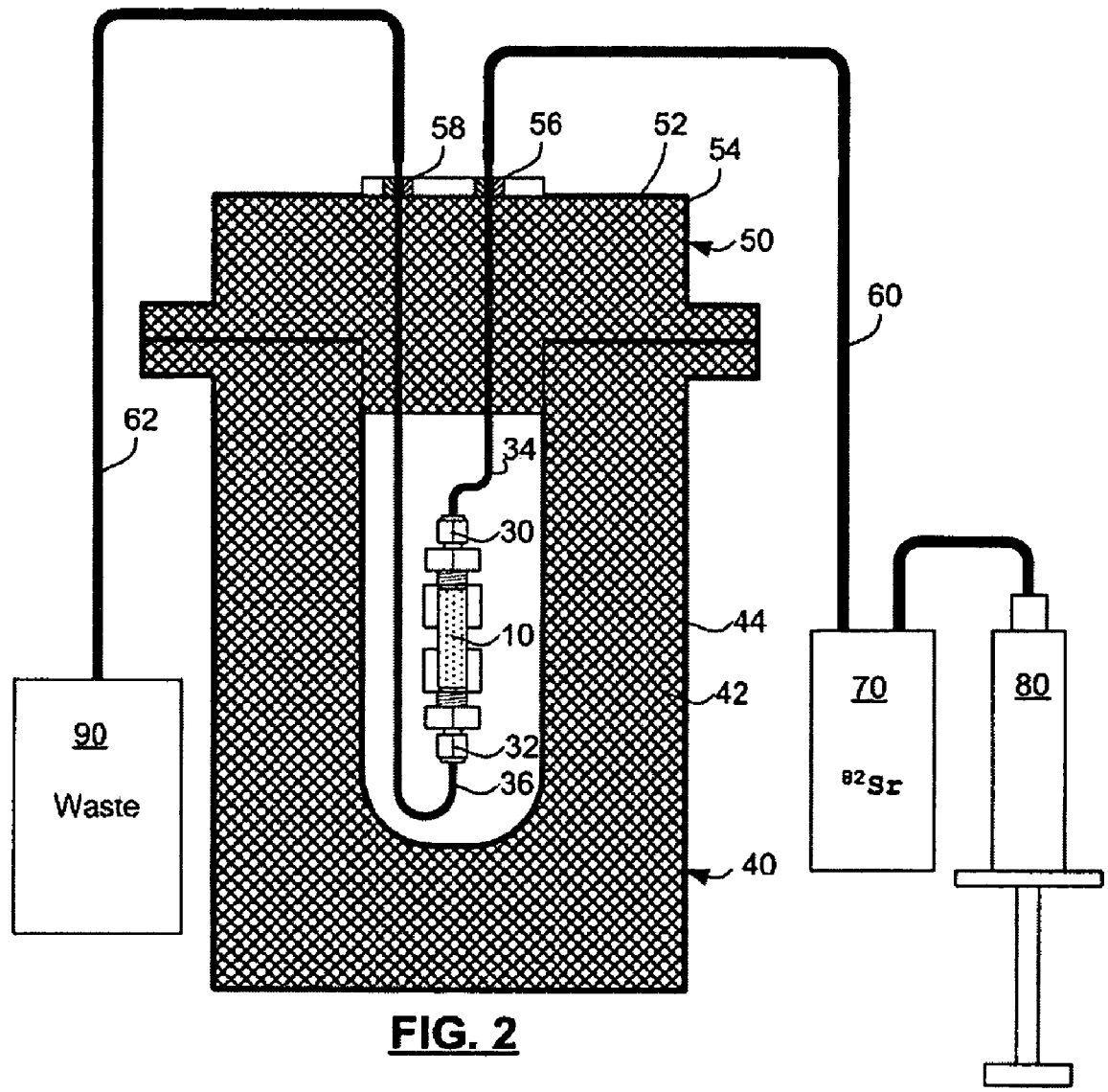
FIG. 2 is a schematic diagram of the generator column shown in FIG. 1 suspended in a shielding body and being loaded with $^{82}$Sr.

FIG. 2 is a cross-sectional view of the generator column 10 suspended in a shielding body 40. The shielding body 40 is made from a dense shielding material 42, such as lead, tungsten or depleted uranium optionally encased in a stainless steel shell 44. The shielding body 42 includes a shielding lid 50 having apertures through which extend an inlet line 34 and outlet line 36. The inlet line 34 is connected to an inlet end 30 of the generator column 10. The outlet line 36 is connected to an outlet end 32 of the generator column 10. The inlet and outlet lines are connected to external tubing lines 60, 62 using Luer fittings 56 and 58. The shielding lid 50 is likewise constructed of a shielding material 52 such as lead, tungsten or depleted uranium encased in a stainless steel shell 54.

After the generator column 10 is packed with ion exchange material 18, as explained above with reference to FIG. 1, the generator column 10 must be loaded with $^{82}$Sr before patient elutions can begin. As schematically illustrated in FIG. 2, in one embodiment a syringe pump 80 is used to deliver $^{82}$Sr from a supply 70 through an inlet tube 60 to the generator column 10. The $^{82}$Sr is bound by the ion exchange material 18 in the generator column 10. Waste fluid is evacuated through the outlet tube 36 and outlet line 62 to a shielded waste container 90, in a manner known in the art.

Figure 3:
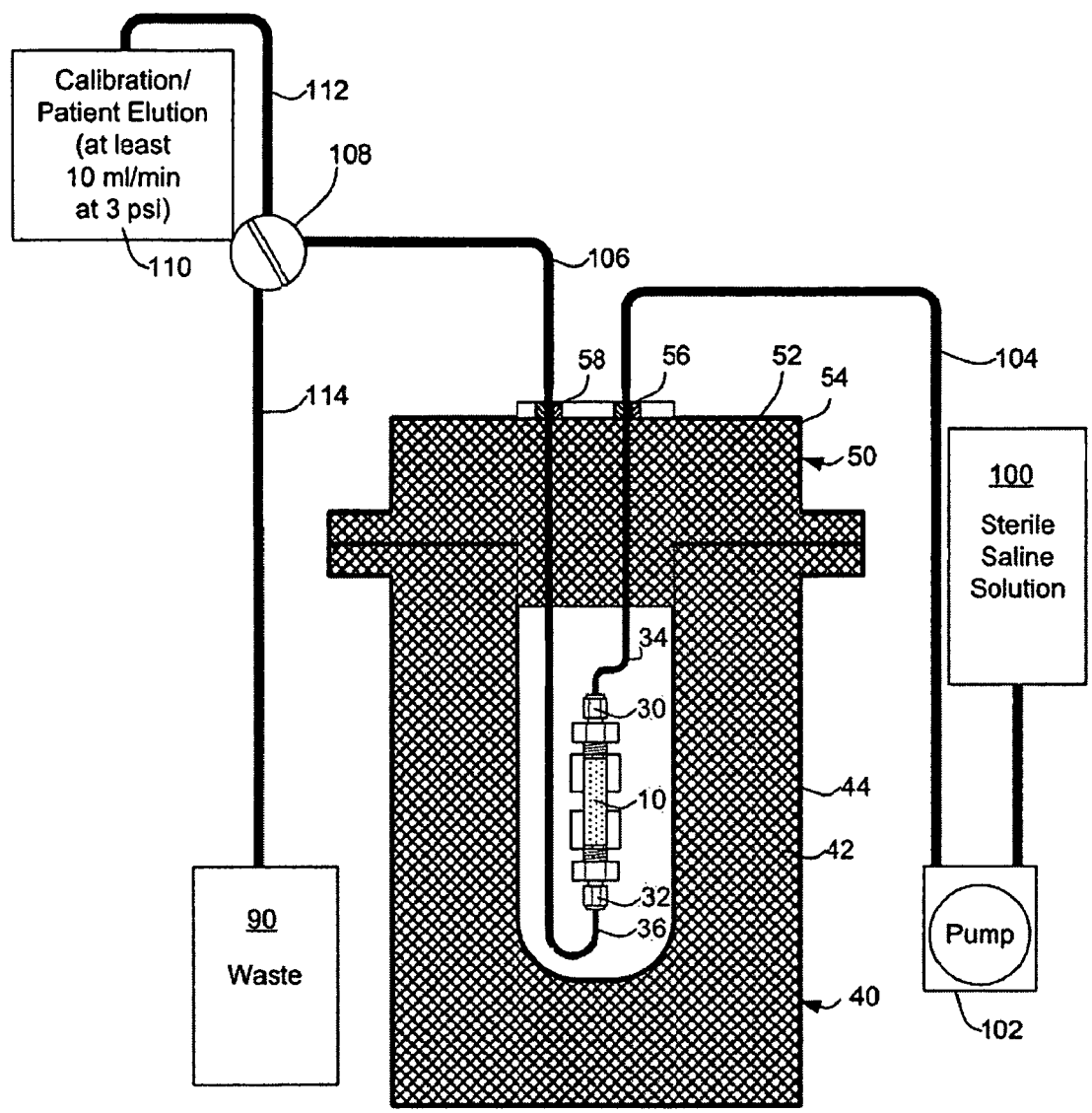
FIG. 3 is a schematic diagram of the generator column shown in FIG. 1 configured for calibration and patient elutions.

FIG. 3 is a schematic diagram of the generator column 10 configured for daily use as an $^{82}$Rb source for cardiac perfusion imaging. A source of sterile saline solution 100 is connected to a saline supply tube 104. The sterile saline solution 100 is pumped through the saline supply tube 104 by a pump 102. In one embodiment of the invention, the pump 102 is a peristaltic pump. In accordance with an alternate embodiment, the pump 102 is the syringe pump 80 shown in FIG. 2.

As understood by those skilled in the art, the pump 102 is controlled by a control algorithm that regulates a flow rate and volume of the sterile saline solution 100 pumped through the generator column 10 via the inlet tube 104 to provide an $^{82}$Rb eluate via an outlet tube 106 connected to a controlled valve 108. The valve 108 directs the eluate through a delivery line 112 for a calibration elution or a patient elution 110, or to a shielded waste container 90. As is further understood by those skilled in the art, control of the system shown in FIG. 3 is complex and not all of the fluid paths and control mechanisms are depicted because elution control is not a subject of this invention.

Figure 4:
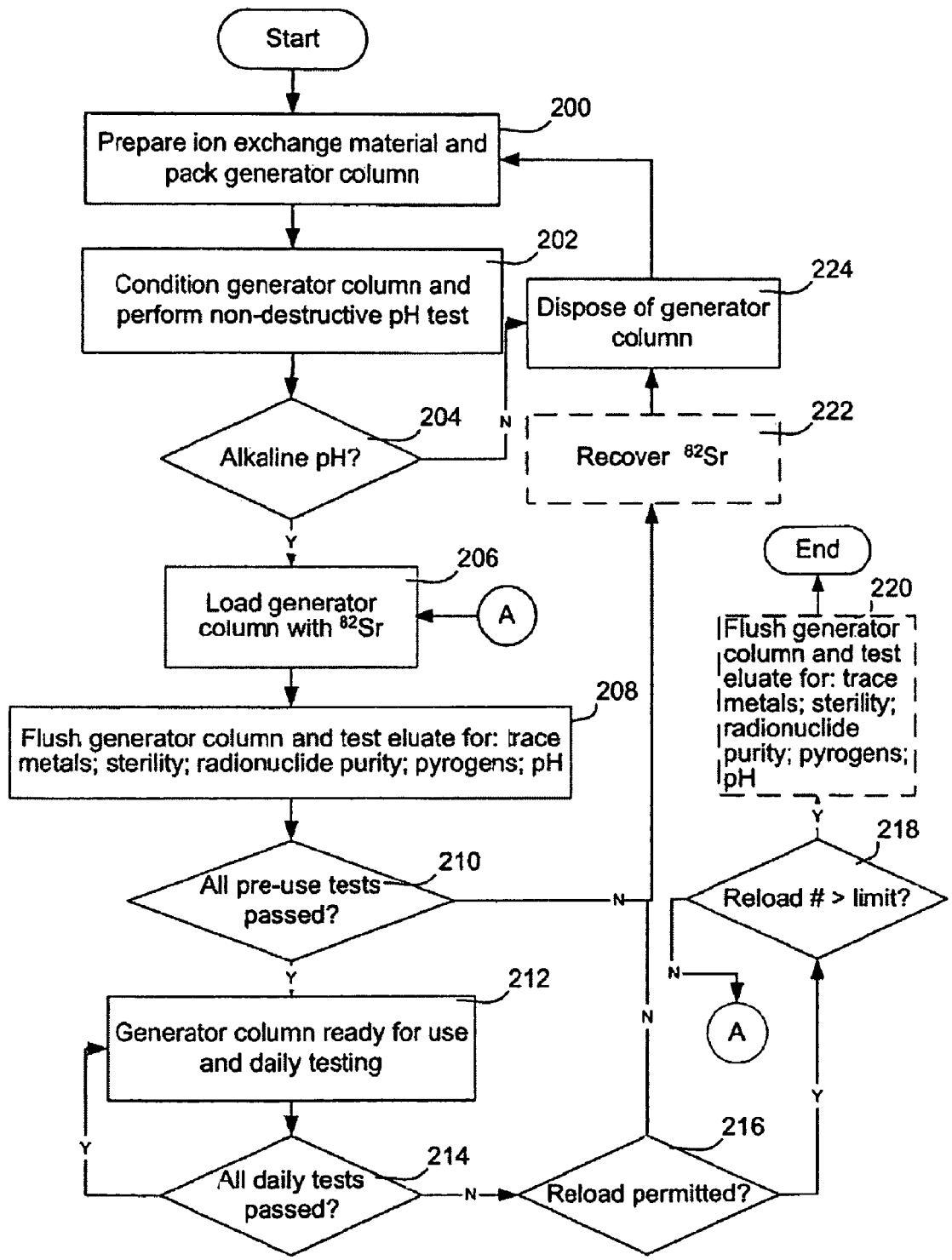
FIG. 4 is a flowchart illustrating the method in accordance with the invention for making the generator columns shown in FIGS. 1-3.

FIG. 4 is a flowchart illustrating principle steps in constructing the generator column 10 in accordance with the invention. The process begins by preparing the ion exchange material and packing the generator column as explained above with reference to FIG. 1 (step 200). The generator column is then conditioned by saturating the ion exchange material 18 with sodium cations. In one embodiment, this is accomplished by passing 120 ml of 2M NaCl through the column at a flow rate of 0.5 ml/minute followed by waiting for a period of 12 hours. 500 ml of sterile saline solution is then passed through the column at a flow rate of 10 ml/minute. A nondestructive pH test is performed (step 202) by testing a pH of the initial sterile saline solution passed through the column. This nondestructive pH test prolongs the life of the generator column 10.

If it is determined (step 204) that the pH of the generator column 10 is not alkaline, the generator column 10 is defective and it is disposed of (step 224). If the saline solution is determined in step 204 to be alkaline, the generator column is loaded with $^{82}$Sr (step 206) in a manner well known in the art using the equipment briefly described above with reference to FIG. 3. After the $^{82}$Sr is loaded into the generator column 10, the generator column 10 is flushed with 1.0 L of sterile saline solution to clear traces of tin: dioxide and any radionuclide impurities. The generator column is then eluted with sterile saline solution and the eluate is tested for trace metals; sterility; radionuclide purity; pyrogens; and pH (step 208). If all of those tests are passed (step 210) the generator column 10 is ready for use (step 212). If any one of the tests fails, $^{82}$Sr is optionally recovered from the generator column 10 (step 222) and the generator column 10 is disposed of (step 224).

During generator use, daily testing is performed for the purpose of patient safety and quality control, as will be described in detail with reference to FIG. 5. As long as all daily tests are passed, the generator column can continue to be used for patient elutions. As understood by those skilled in the art, one of the daily tests is a measure of $^{82}$Rb yield. If it is determined in step 214 that one of the daily tests failed, it is further determined whether a reload of the generator column 10 is permitted (step 216). Reloading is permitted if the daily test failed due insufficient $^{82}$Rb yield only. If the daily test failed for some other reason the generators column 10 cannot be further used, and the $^{82}$Sr is optionally recovered (step 222) before the generator column is disposed of (step 224), as described above. If an $^{82}$Sr reload is permitted, it is determined in step 218 whether the number of $^{82}$Sr reloads of the generator column 10 has exceeded a predetermined reload limit. A generator column in accordance with the invention can, be loaded with $^{82}$Sr at least three times before any significant $^{82}$Sr breakthrough occurs. If it determined in step 218 that the reload limit has been reached, certain jurisdictions require that the generator column be flushed and the eluate tested for: trace metals; sterility; radionuclide purity; pyrogens; and pH. If it is determined in step 218 that the reload limit, has not been reached, the process branches back to step 206 and the generator column is reloaded with $^{82}$Sr and steps 208-218 are repeated.

Figure 5:
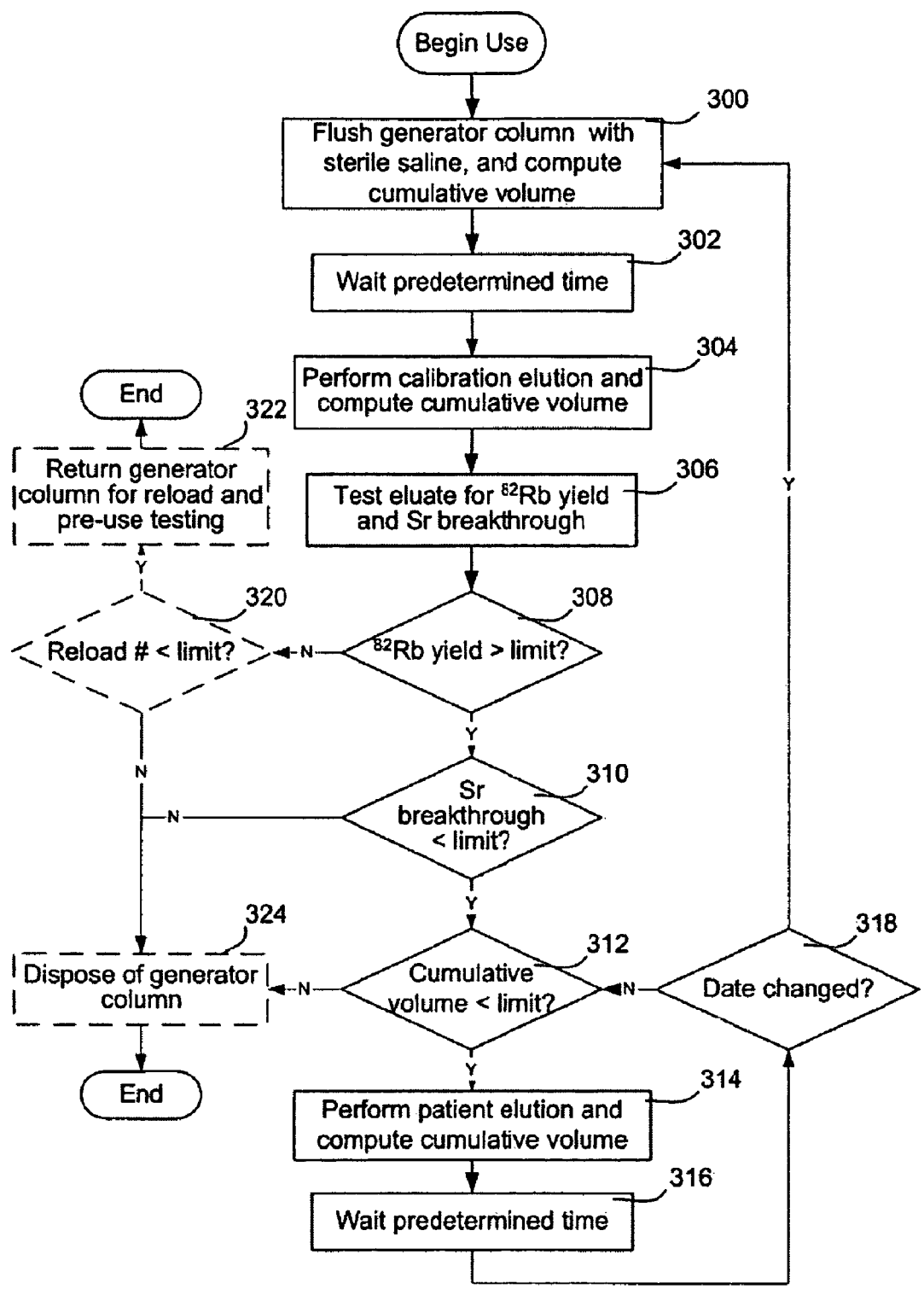
FIG. 5 is a flowchart illustrating principle steps in the use of the generator column shown in FIG. 3.

FIG. 5 is a flowchart illustrating principle steps involved in the daily use of the generator column 10 in accordance with the invention. Prior to each day's use of the generator column 10, the generator column 10 is flushed with 50 ml of sterile saline solution (step 300) in order, to remove any strontium breakthrough from the generator column 10 into the waste vessel 90. The operator then waits for a predetermined period of time (step 302) before performing a calibration elution (step 304). As is well understood by those skilled in the art, under stable conditions the generator column maintains a $^{82}Sr/^{82}Rb$ equilibrium which is achieved after about 10 minutes. Consequently, the predetermined wait before a calibration elution is performed is at least 10 minutes. After the required wait, the generator column is eluted with about 15 ml of sterile saline solution at a constant flow rate of about 15 ml/minute. The calibration eluate is tested (step 306) for $^{82}Rb$ yield and $^{82}Sr$ breakthrough. In step 308 it is determined whether the yield is above a predetermined radioactivity limit. As is understood by those skilled in the art, the half life of $^{82}Rb$ is very short (i.e. 76 seconds). Consequently, in one embodiment the $^{82}Rb$ yield is measured using a positron counter during the elution, in a manner well known in, the art.

In step 310, it is determined whether the $^{82}Sr$, $^{85}Sr$ breakthrough is less than a predetermined breakthrough limit. As is also understood by those skilled in the art, all jurisdictions define a threshold for permissible levels of $^{82}Sr$, $^{85}Sr$ breakthrough. As is further understood by those skilled in the art, the strontium breakthrough is readily determined by testing the radioactivity of the elution after about 26 minutes has elapsed, at which time the amount of residual $^{82}Rb$ is insignificant and does not distort the test results.

Before daily use begins, a cumulative volume of all fluids flushed and eluted through the generator column 10 is computed. Since the generator column 10 in accordance with the invention is repeatedly reloaded with $^{82}Sr$, each generator column is identified by a unique identifier, in one embodiment a serial number. If the user of a generator column 10 does not have the facility to reload the generator column 10, the user must return the generator column 10 to the manufacturer, along with a cumulative total of fluid flushed and eluted through the column during that use. Likewise, when a reloaded column is supplied to a user, a cumulative volume of fluid used to flush and elute the column during all prior reload(s) and use(s) is provided to the user. Control software used to control a volume of fluid used during generator column 10 flushes and elutions accepts the cumulative volume and stores it. The control software then recomputes the cumulative volume after each subsequent flush or elution of the generator column 10. That computed cumulative volume is compared (step 312) to a predefined volume limit. In accordance with one embodiment of the invention, empirical data has shown that 10 to 30 litres of sterile saline solution 100 can be pumped through the generator column 10 before significant $^{82}Sr$ breakthrough is experienced, so the volume limit may be set between 10 and 30 litres.

If each of the tests 308-312 is successfully passed, patient elutions (step 314) may be performed in a manner well known in the art. After each elution, it is necessary to wait a predetermined period of time, about 5 to 10 minutes, (step 316) to permit $^{82}Rb$ to regenerate. After each elution, the cumulative volume is recomputed by adding to the cumulative volume a volume of fluid pumped through the generator column 10 during the patient elution. Then it is determined whether the control system date has, changed, i.e. a new day has begun (step 318). If not, the cumulative volume is compared to the predetermined volume limit. If the volume limit has been exceeded, the generator column is disposed of (step 324).

If it is determined in step 318 that the control system date has changed, the generator column 10 must be flushed and re-tested per steps 300-312, as described above. If those tests determine that the $^{82}Rb$ yield is less than a predetermined limit (step 308) then it is determined in step 320 whether the reload limit has been exceeded and if not the generator column 10 is returned for reload and pre-use testing (step 322). Otherwise, the generator column is disposed of (step 324). It should be noted that if any of tests 308-312 fail, the generator column 10 may be returned to the manufacturer who determines whether the generator column 10 can be reloaded (step 320) and disposes of the generator column 10 (step 324) if it cannot be reloaded.

The generator column 10 in accordance with the invention reduces the expense of cardiac perfusion imaging while ensuring compatibility with 3D PET imaging systems by enabling low pressure, low flow rate elutions that can be precisely flow controlled. Research has conclusively established that the generator column 10 in accordance with the invention remains sterile and pyrogen-free for a period of at least six months when used in accordance with the procedures and limits described above.

Although the invention has been explained with reference to 3D PET imaging systems, it should be understood that the generator column 10 is equally compatible with 2D PET imaging systems and provides the same advantages of low cost, precise flow control, low pressure and low flow elution and a long service life.

The embodiment(s) of the invention described above is(are) intended to be exemplary only. The scope of the invention is therefore intended to be limited solely by the scope of the appended claims.

I claim:

1. An $^{82}Sr/^{82}Rb$ generator column for use with a peristaltic pump, comprising:
   a cylindrical container of fluid impervious material having a cover for closing the container in a fluid tight seal, and further having an inlet for connection of a conduit for delivering a fluid into the container and an outlet for connection of a conduit for conducting the fluid from the container; and
   an ion exchange material filling the container, the ion exchange material being compacted within the container to a density of not more than 3 g/cm$^3$ that permits the ion exchange material to be eluted at a flow rate of at least 5 ml/min at fluid pressure of 1.5 pounds per square inch (10 kPa).

2. The $^{82}Sr/^{82}Rb$ generator column as claimed in claim 1 wherein the ion exchange material comprises α-hydrous tin dioxide.

3. The $^{82}Sr/^{82}Rb$ generator column as claimed in claim 2 wherein a total volume of the α-hydrous tin dioxide in the generator column is about 1.5 cm$^3$.

4. The $^{82}Sr/^{82}Rb$ generator column as claimed in claim 1 further comprising a particle filter at each of the inlet and the outlet.

5. The $^{82}Sr/^{82}Rb$ generator column as claimed in claim 1 further comprising a peristaltic pump for flushing and eluting the generator column.

* * * * *